United States Patent
Serban et al.

(10) Patent No.: US 8,563,319 B2
(45) Date of Patent: *Oct. 22, 2013

(54) DIFFERENTIAL RESONATORS FOR $NO_2$ DETECTION AND METHODS RELATED THERETO

(75) Inventors: Bogdan Catalin Serban, Bucharest (RO); Cornel P. Cobianu, Bucharest (RO); Mihai N. Mihaila, Bucharest (RO); Viorel Georgel Dumitru, Ploiesti (RO); Octavian Buiu, Bucharest (RO)

(73) Assignee: Honeywell Romania S.R.L., Bucharest (RO)

(*) Notice: Subject to any disclaimer, the term of this patent is extended or adjusted under 35 U.S.C. 154(b) by 321 days.

This patent is subject to a terminal disclaimer.

(21) Appl. No.: 12/962,067

(22) Filed: Dec. 7, 2010

(65) Prior Publication Data

US 2011/0143447 A1    Jun. 16, 2011

(30) Foreign Application Priority Data

Dec. 11, 2009  (EP) ..................... 09178792

(51) Int. Cl.
*G01N 33/00*  (2006.01)
*G01N 29/36*  (2006.01)

(52) U.S. Cl.
USPC ............. 436/117; 422/82.01; 422/82.02; 422/82.03; 422/82.04; 422/83; 422/88; 422/98; 436/116; 436/118

(58) Field of Classification Search
USPC ............... 422/82.01–82.04, 83, 88, 98; 436/116–118
See application file for complete search history.

(56) References Cited

U.S. PATENT DOCUMENTS

| | | | |
|---|---|---|---|
| 5,552,274 A * | 9/1996 | Oyama et al. | 435/6.12 |
| 5,932,953 A * | 8/1999 | Drees et al. | 310/324 |
| 6,355,498 B1 * | 3/2002 | Chan et al. | 438/48 |
| 6,866,819 B1 * | 3/2005 | Chandra et al. | 422/50 |

(Continued)

FOREIGN PATENT DOCUMENTS

| | | |
|---|---|---|
| EP | 0072744 A2 | 2/1983 |
| WO | WO-2008088780 A1 | 7/2008 |

OTHER PUBLICATIONS

Cobianu, C., et al., "Nano-scale resonant sensors for gas and bio detection: Expectations and challenges", International Semiconductor Conference, 2009. CAS 2009., XP031568982 ISBN : 978-1-4244-441,3-7, (2009), 259-262.

(Continued)

*Primary Examiner* — Arlen Soderquist
(74) *Attorney, Agent, or Firm* — Schwegman, Lundberg & Woessner, P.A.

(57) ABSTRACT

A nitrogen dioxide sensor comprising a first beam having a first functionalized sensing surface capable of sensing nitrogen dioxide, the first beam capable of producing a first resonant frequency; and a second beam having a second functionalized reference surface not capable of sensing nitrogen dioxide, the second beam capable of producing a second resonant frequency, wherein differential sensing of nitrogen dioxide may be performed, further wherein the first beam and the second beam are each functionalized with one or more soft bases having comparable viscoelastic properties is provided. In one embodiment, the sensor is a nano-sensor capable of low drift and accurate detection of nitrogen dioxide levels at the zeptogram level. Methods of making and using a nitrogen dioxide sensor are also provided.

22 Claims, 2 Drawing Sheets

(56) References Cited

U.S. PATENT DOCUMENTS

| | | | |
|---|---|---|---|
| 7,280,078 B2* | 10/2007 | Salsman et al. | 343/703 |
| 7,340,941 B1* | 3/2008 | Fruhberger et al. | 73/24.01 |
| 7,409,851 B2* | 8/2008 | Ilic et al. | 73/24.06 |
| 7,691,583 B2* | 4/2010 | Craighead et al. | 435/7.1 |
| 7,694,346 B2* | 4/2010 | Adams et al. | 850/7 |
| 7,770,449 B2* | 8/2010 | Chen et al. | 73/335.05 |
| 7,871,569 B2* | 1/2011 | Zhang et al. | 422/68.1 |
| 7,892,759 B2* | 2/2011 | Mutharasan et al. | 435/7.1 |
| 7,914,740 B2* | 3/2011 | Zhang et al. | 422/68.1 |
| 7,935,191 B2* | 5/2011 | Mutharasan et al. | 134/1 |
| 7,959,873 B1* | 6/2011 | Roukes et al. | 422/400 |
| 7,972,865 B2* | 7/2011 | Yi et al. | 436/149 |
| 8,168,120 B1* | 5/2012 | Younis | 422/82.01 |
| 8,220,067 B2* | 7/2012 | Adams et al. | 850/56 |
| 8,230,720 B2* | 7/2012 | Serban et al. | 73/24.01 |
| 8,291,745 B2* | 10/2012 | Karabacak et al. | 73/24.01 |
| 2003/0215865 A1* | 11/2003 | Mayer et al. | 435/6 |
| 2004/0093947 A1* | 5/2004 | Brederlow et al. | 73/590 |
| 2004/0150296 A1* | 8/2004 | Park et al. | 310/324 |
| 2006/0196253 A1* | 9/2006 | Crawley et al. | 73/53.01 |
| 2006/0257286 A1* | 11/2006 | Adams | 422/82.01 |
| 2008/0110247 A1 | 5/2008 | Shaw et al. | |
| 2008/0116490 A1* | 5/2008 | Stewart et al. | 257/210 |
| 2010/0000292 A1* | 1/2010 | Karabacak et al. | 73/24.01 |
| 2010/0055801 A1* | 3/2010 | Yi et al. | 436/149 |
| 2010/0129920 A1* | 5/2010 | Mortet et al. | 436/94 |
| 2010/0282245 A1* | 11/2010 | Star et al. | 128/200.14 |
| 2011/0113856 A1 | 5/2011 | Cobianu et al. | |
| 2011/0116974 A1* | 5/2011 | Serban et al. | 422/88 |
| 2011/0143448 A1* | 6/2011 | Serban et al. | 436/122 |
| 2012/0094270 A1* | 4/2012 | Mutharasan et al. | 435/5 |

OTHER PUBLICATIONS

Durand, C, et al., "In-Plane Silicon-On-Nothing Nanometer-Scale Resonant Suspended Gate MOSFET for In-IC Integration Perspectives", IEEE Electron Device Letters, 29(5), XP0L1207042 ISSN: 0741-3106, (2008), 494-496.

Cobianu, C., et al., "All-Differential Resonant Nanosensor Apparatus and Method", U.S. Appl. No. 12/617,893, filed Nov. 13, 2009, 23 pgs.

* cited by examiner

DIFFERENTIAL RESONATORS FOR NO$_2$ DETECTION AND METHODS RELATED THERETO

RELATED MATTERS

This application claims priority under 35 USC §119 to European Application Serial Number 09 178792.9, filed Dec. 11, 2009, which is incorporated herein by reference in its entirety.

BACKGROUND

Reduction of toxic gas emissions requires not only an increase in efficiency of energy-intensive activities, but also a limit on the permissible amount of green house gases (GHG) and toxic gases released by manufacturers. With respect to nitrogen dioxide (NO$_2$), the U.S. National Ambient Air Quality (NAAQS) Standards set the permissible annual amount of such emissions at a maximum of 53 parts per billion (ppb), with short term exposures limits (STEL) at one (1) parts per million (ppm) for 15 minute exposures.

SUMMARY

The inventors recognize the need for providing gas sensing devices with reduced drift, improved accuracy and high sensitivity. Additionally, the inventors recognize the need for providing gas sensing devices which can accurately detect NO$_2$ emissions in ranges smaller than parts per million (ppm) in the ambient. The novel sensors described herein provide improved accuracy together with the ability to detect ultra small gas concentrations on the order of parts per billion (ppb), parts per trillion (ppt) or smaller. In other embodiments, the devices may be used in micro-scale electromechanical systems.

A nitrogen dioxide sensor comprising a first beam having a first functionalized sensing surface capable of sensing nitrogen dioxide, the first beam capable of producing a first resonant frequency; and a second beam having a second functionalized reference surface not capable of sensing nitrogen dioxide, the second beam capable of producing a second resonant frequency, wherein differential sensing of nitrogen dioxide may be performed is provided.

In one embodiment, the second functionalized reference surface is further altered with respect to a first beam by adding a polyethylene coating to prevent detection of NO$_2$.

In one embodiment, the sensor has low drift, as compared to conventional differential resonant sensors, which use bare surfaces on the second beam. In general, a "low drift" sensor refers to a sensor with a baseline drift which is at least five times lower than the sensor resolution itself, thus allowing the sensor to preserve its accuracy within its entire dynamic range, for its entire sensor lifetime. In one embodiment, the sensor is capable of accurate detection of nitrogen dioxide levels at the zeptogram level.

In one embodiment, the sensor is a nanosensor capable of performing differential sensing by monitoring changes in the resonant frequency of the first beam relative to the resonant frequency of the second beam. The first and second beams of the sensor may be located on a single silicon substrate or on different silicon substrates.

The first and second beams may be functionalized in any suitable manner, such as with one or more soft bases (e.g., a conjugated aromatic hydrocarbon, a carbon nanotube, and a ferrocene moiety), each having comparable visco-elastic properties. In one embodiment, each beam is functionalized with a different soft base.

The first beam of the sensor may have a functionalized surface containing carbon nanotube moieties as sensitive groups for nitrogen dioxide detection bonded downward to C=O and linked to the functionalized surface by carbon atoms, while the second beam may have a functionalized surface containing a coating of polyethylene to prevent detection of nitrogen dioxide, the coating of polyethylene deposited above the sensing monolayer, which is also present on the first beam.

The first beam of the sensor may have a functionalized surface containing ferrocene moieties as sensitive groups for nitrogen dioxide detection, while the second beam may have a functionalized surface further containing a coating of polyethylene to prevent detection of nitrogen dioxide.

In one embodiment, the sensor further comprises a first frequency measuring circuit for measuring the resonant frequency of the first beam; a second frequency measuring circuit for measuring the resonant frequency of the second beam: and a control for analyzing the signals from the first frequency measuring circuit and the second frequency measuring circuit, wherein a differential frequency equivalent to the first frequency minus the second frequency is determinable, wherein differential sensing of nitrogen dioxide exposure is performed.

Embodiments of the invention further comprise a method comprising functionalizing a silicon surface to detect NO$_2$; and altering a portion of the functionalized silicon surface to prevent detection of NO$_2$. In one embodiment, the silicon surface is functionalized with carbon nanotube moieties by first preparing an amino-terminated silicon surface or an iodine-terminated silicon surface. In one embodiment, the silicon surface is functionalized through reaction of carboxylic carbon nanotubes with an alcohol-terminated silicon surface in the presence of dicyclohexyl carbodiimide in DMSO. In one embodiment, the silicon surface is functionalized through reaction of a compound synthesized by reacting carbon nanotubes with allyl iodide and potassium and hydrogen terminated silicon surfaces. In these embodiments, a portion of the functionalized silicon surface has been altered to prevent detection of nitrogen dioxide is altered by direct printing of a polyethylene coating.

In one embodiment, the invention further comprises connecting frequency measuring circuits to a suspended vibrating beam (e.g., clamped-clamped silicon beam, cantilever, silicon nanowire as a portion of a silicon chip) containing the functionalized silicon surface in order to produce differential resonance frequency changes; connecting inputs of a mixer to the output of the frequency measuring circuits to measure the differential resonance frequency changes; and outputting the differential resonance frequency changes to a presentation device.

Embodiments of the invention further comprise a method of detecting nitrogen dioxide comprising exposing first and second beams to nitrogen dioxide, wherein the first beam has a functionalized surface to detect nitrogen dioxide and the second beam has a functionalized surface altered to prevent detection of nitrogen dioxide; and comparing the resonance frequency of the first beam to the resonance frequency of second beam, wherein an amount of nitrogen dioxide exposure is determined. In one embodiment, the first and second beams are nano-beams and the second beam is altered with a polyethylene coating.

Embodiments of the novel NO$_2$ gas sensors described herein are low in cost and high in performance with low drift detection capabilities and excellent mass resolution. In one embodiment, resonant differential principles are applied to silicon nano-electromechanical systems (NEMS), thus allowing for detection in the range of hundreds of zeptograms of $NO_2$, with baseline drift elimination.

DETAILED DESCRIPTION

Figure 1:
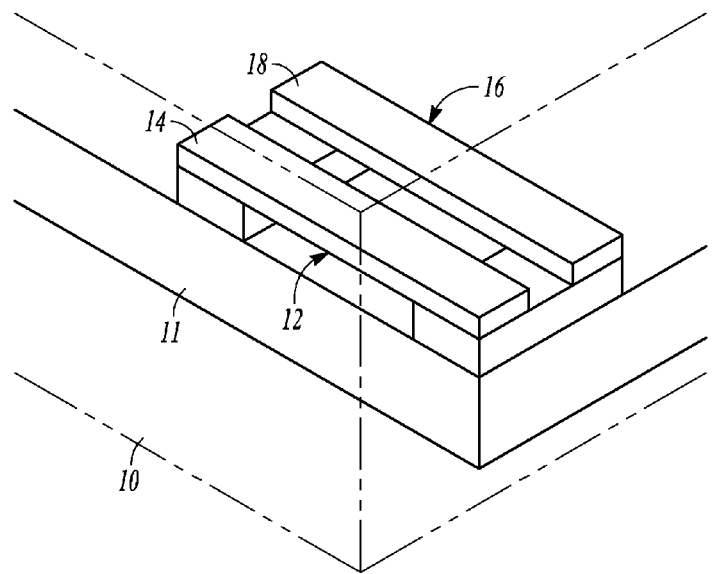
FIG. 1 is a simplified illustration of a nitrogen dioxide ($NO_2$) resonator according to an example embodiment.

In the following description, reference is made to the accompanying drawings that form a part hereof, and in which is shown by way of illustration specific embodiments which may be practiced. These embodiments are described in sufficient detail to enable those skilled in the art to practice the invention, and it is to be understood that other embodiments may be utilized and that structural, chemical and procedural changes may be made without departing from the scope of the present invention. The following description of example embodiments is, therefore, not to be taken in a limited sense, and the scope of the present invention is defined by the appended claims.

The Detailed Description that follows begins with a brief overview of conventional differential sensing devices, a description of the embodiments and a brief conclusion.

Conventional Differential Bio-Chemical Sensing Devices

Conventional differential bio-chemical sensing devices based on the resonance principle may include a resonant sensing loop, a resonant reference loop and an electronic mixer which outputs the difference between the resonance frequencies provided by each of the sensing and reference loops. Both loops comprise an identical electronic readout circuit for frequency measurement and a device to determine the resonance frequency. The resonant sensing loop comprises a device exposed to the external environment to be monitored, i.e. a bio-chemical resonant sensor having a functionalized surface or a sensing layer chemically designed to adsorb or absorb and detect the desired bio-chemical component (gas or bio component), by its reversible reaction with the functionalized surface.

The resonant reference loop in these prior art differential bio-chemical resonant sensors comprises a "vibrating" device with the same geometry as the sensor, but having a bare surface or an uncoated surface. As a result, the prior art bare (uncoated) surface is likely to have a different response to external conditions (e.g., humidity in the ambient air, temperature, ageing, and the like) as compared to the sensing layer. Thus, when the resulting signals of the sensing and reference loop are sent through the mixer for comparison, the effect of this external effect, such as humidity, are not eliminated.

Additionally, if the visco-elastic properties of the functionalized sensing layer are changing over time, the resonance frequency of the sensing loop is influenced. Therefore, in the prior art, when making the frequency subtraction, these ageing influences cannot be subtracted from the mixer's response, as these effects are not present in the uncoated reference device.

Therefore, the "common mode signals" such as humidity, ageing of the sensing layer, and the like, cannot be eliminated at the mixer level, as they are not present in both terms to be subtracted. Such influences, i.e., susceptibility to external effects, result in a significant amount of "baseline drift," leading to reduced accuracy. Additionally, the prior art sensors are only able to discern gaseous levels in the parts per million (ppm) range.

DESCRIPTION OF THE EMBODIMENTS

In contrast, embodiments of the present invention comprise a bio-chemical differential sensor with a resonant reference loop comprising a functionalized reference layer on the reference beam surface with visco-elastic properties similar to the functionalized sensing layer, but altered (such as with a coating) to provide a functionalized reference beam having no sensing properties. Use of a non-sensing functionalized reference surface in the reference loop allows, for the first time, full scale differential sensing which is not only highly accurate and drift-free, but capable of discerning $NO_2$ content in extremely small amounts of $NO_2$, such as in the zeptogram range.

FIG. 1 illustrates an example of nitrogen dioxide sensor 10. The nitrogen dioxide sensor 10 includes a substrate 11 with a first beam 12 and a second beam 16 formed on the substrate 11. Although the first and second beams 12, 16 are shown on the same substrate 11, embodiments are contemplated where the first and second beams 12, 16 could be also on different substrates.

Figure 2:
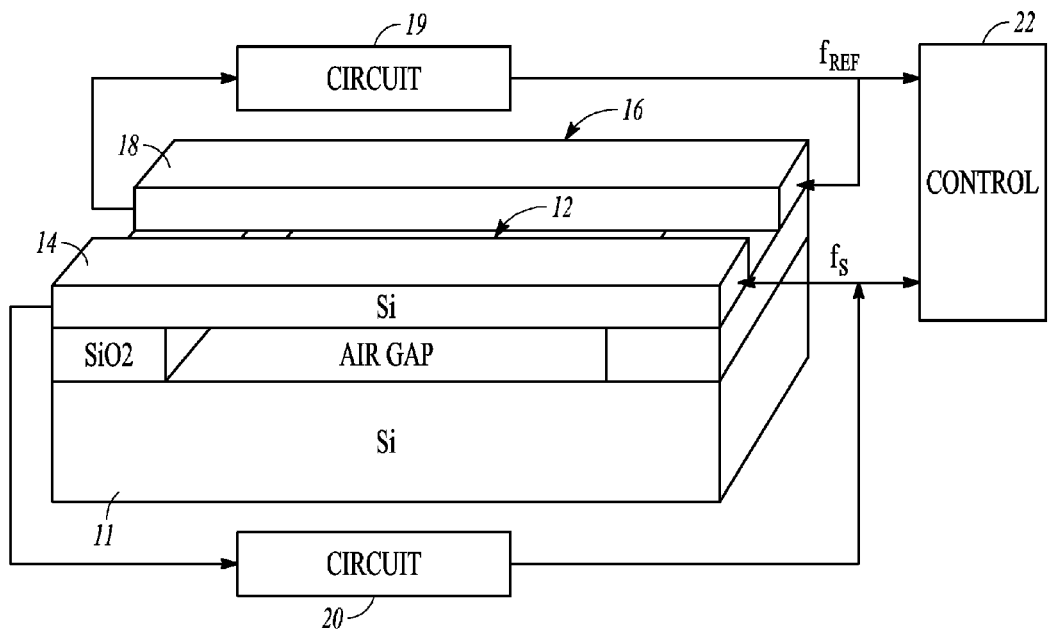
FIG. 2 is an enlarged view illustrating a portion of the $NO_2$ sensor shown in FIG. 1 according to an example embodiment.

FIG. 2 is an enlarged view illustrating a portion of the nitrogen dioxide sensor shown in FIG. 1. The first beam 12 includes a first functionalized sensing surface (i.e., first sensing monolayer 14 and the second beam 16 includes a second functionalized reference layer 18 (i.e., a coating layer deposited on top of the same functionalized monolayer applied on both first and second beam). Each of the functionalized sensing and reference surfaces 14 and 18, respectively possess similar visco-elastic properties and ageing properties and will respond similarly to ambient temperature and humidity (e.g., similar hydrophilic or hydrophobic properties).

A "functionalized surface" refers herein to a beam surface modified in a manner to perform a desired function, i.e., to either sense (and thus to obtain a sensing beam) or to not sense (and thus obtain a reference beam) by means of monolayers grown or applied on the beam. However, embodiments are contemplated in which the first and second sensing and reference functionalized surfaces, 14 and 18, respectively are each functionalized in a different manner according to any suitable method, such as any one of Schemes 1-5 described herein. The functionalized surfaces 14, 18 may be part of the first and second beams 12, 16, respectively or formed as part of a layer or coating further added to the initially modified surface of the second beam 16, to obtain a first functionalized sensing beam 12 and a functionalized non-sensing reference beam 16. Thus, a functionalized surface may be altered by some method to inhibit sensing or detection of nitrogen dioxide on the second beam 16. In an illustrated example embodiment, the second functionalized reference surface 18, however, has further been altered through deposition of a coating or barrier layer to prevent the second functionalized reference surface 18 from sensing $NO_2$, thus allowing the second functionalized reference surface 18 to function as a non-sensing functionalized reference surface.

In use, the nitrogen dioxide sensor 10 performs differential sensing of nitrogen dioxide by monitoring changes in the resonant frequency of the first beam 12 relative to the resonant frequency of the second beam 16. Therefore, the nitrogen dioxide sensor 10 may further include a first frequency measuring device 20 for measuring the resonant frequency of the first beam 12 and a second frequency measuring device 19 for measuring the resonant frequency of the second beam 16.

The frequency measuring circuits 19 and 20 may operate, for example, according to the principle of phase lock loop circuits. (See, for example, U.S. Pat. No. 6,722,200, (hereinafter '200), which is hereby incorporated by reference in its entirety). Each of the circuits 19 and 20 provide the resonance frequency of the corresponding beams. In one embodiment, the invention provides an all differential resonant sensor, where the resonance frequencies of the two beams are subtracted at the level of an electronic reader, in order to get a frequency difference which will eliminate the common mode signal due to humidity, ageing, etc, as is discussed in U.S. patent application Ser. No. 12/617,893 entitled, "All-Differential Resonant Nanosensor Apparatus and Method, filed on Nov. 13, 2009 (hereinafter "'893), which is hereby incorporated by reference herein in its entirety.

A differential reading electronic circuit, comprising a mixer with the two frequency signals at the input and with the frequency difference at the output may be interconnected with each resonant beam pair (sensing and reference) for signal processing. By subtracting the frequency response from the sensing loop and the reference loop, a drift-free frequency signal for $NO_2$ may be obtained. If desired, two electronic oscillators may be used for the reading of the two resonance frequencies. In this case, each oscillator is made of an amplifier having in its feed-back loop a vibrating beam.

Figure 3:
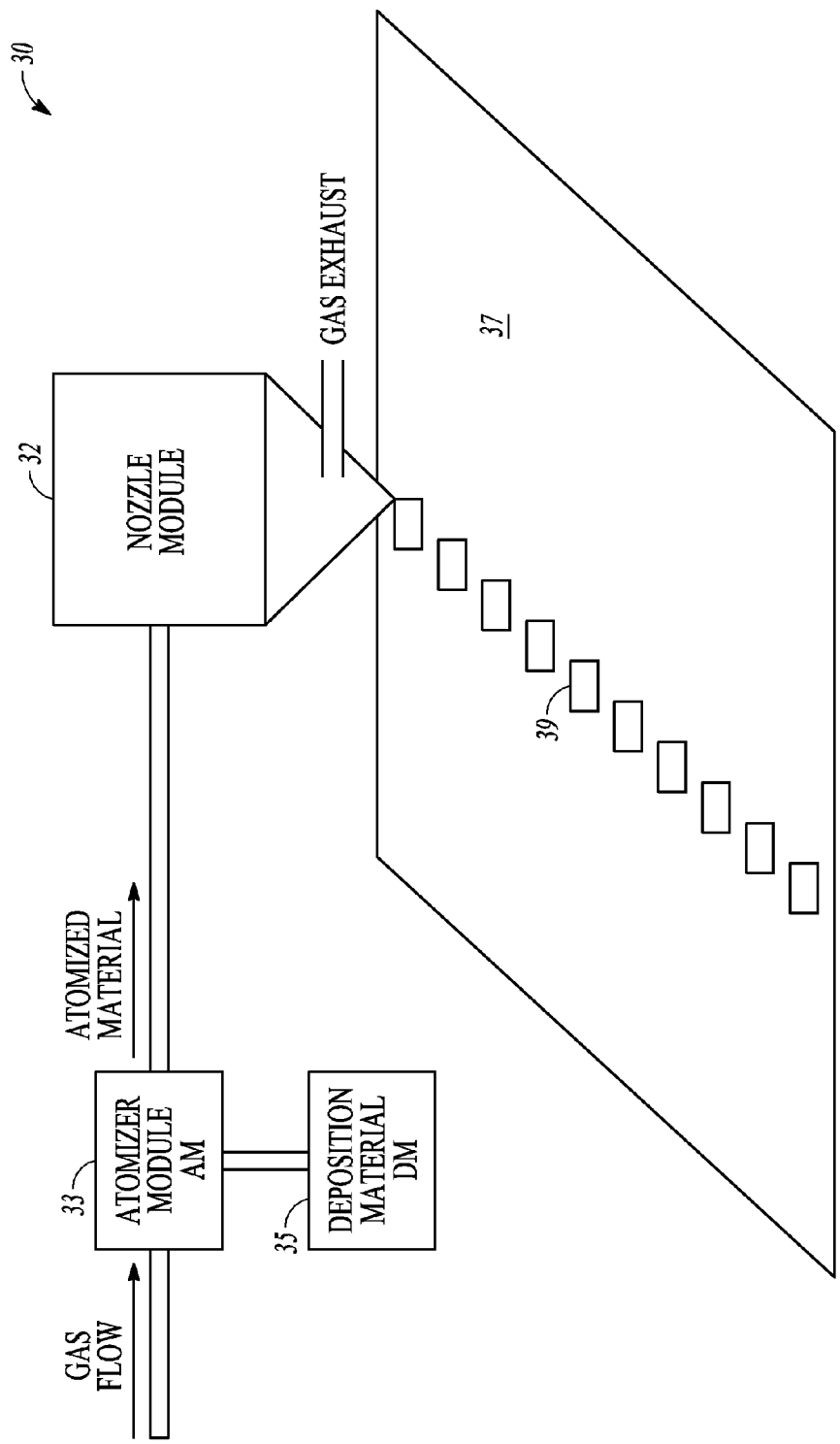
FIG. 3 is a simplified illustration of a direct printing system for preparing a functionalized surface according to an example embodiment.

The first and second frequency measuring circuits 19, 20 may be a variety of electronic circuits. In one embodiment, the first and second frequency measuring circuits 19, 20 are similar to the circuits disclosed in U.S. Pat. No. 6,722,200, which is hereby incorporated by reference in its entirety. In some embodiments, the first and the second frequency measuring circuits 19, 20 send signals to a mixer or control 22 for differential sensing as described in '893, supra. Specifically, as mentioned above, at the output of the mixer 22, the difference of the frequencies measured by the two frequency measuring circuits 19 and 20. The frequency difference will give a drift free, high accuracy information about the gas to be detected In one embodiment, the devices and methods described herein are compatible with conventional integrated circuit (IC) processing, as this term is understood in the art. FIG. 3 is an illustration of one embodiment of a single head direct printing system 30 useful herein. In this system 30, deposition material (DM) 35 uses a distribution system for local, selective and additive direct deposition of the desired material. For example, the print head 32 may be supplied with atomized DM from a an atomizer module (AM) 33 connected to a DM source 35 and a suitable gas supply, as is known in the art, for deposition of the atomized DM 33 on a silicon surface (e.g., wafer) 37 to form a functionalized reference layer 39 (such as an ultra thin reference layer) on the silicon wafer 37 as shown in FIG. 3. As noted above, the silicon surface 37 may comprise any configuration and size of silicon substrate. In the embodiment shown in FIGS. 1 and 2, for example, such a deposit would be present only on each second beam 16 of a chip.

The DM 35 necessarily comprises a material chemically designed to essentially "de-functionalize" the second functionalized sensing surface. 42, to produce a non-sensing functionalized reference surface.

In one embodiment, DM 35 may be polyethylene. Such a coating alters the functionalized sensing surface. The coating is dispensed selectively and without use of a mask on the existing functionalized sensing layer already present. Referring again to FIGS. 1 and 2, this functionalized layer is located on the reference beam 16.

Direct printing may be considered a type of post-processing performed on a silicon substrate, such as a wafer, prior to subsequent steps, such as packaging and dicing. Through use of selective additives as described herein, there is now no need for post-print etching.

In one embodiment, methods for on-wafer functionalization of a differential $NO_2$ resonant nano-sensor containing a tandem of a sensing monolayer obtained on the surface of a Si vibrating beam and a reference (non-sensing) monolayer obtained on the surface of a Si reference vibrating beam, both vibrating beams being located on the same chip and being excited to resonance and interrogated with identical electronics is provided. In one embodiment, by applying a barrier layer or coating, such as a polyethylene coating on the reference beam, a non-sensing reference beam is obtained. In one embodiment, the polyethylene coating is applied by direct selectively printing of liquid polyethylene, which may be further thermally treated to get a solid state ultra thin coating (i.e., such as between about three (3) up to no more than about five (5) nanometers (nm) in thickness, although portions of the coating may exceed five (5) nm), thereby creating the non-sensing functionalized reference beam.

In one embodiment, functionalization of all the Si surfaces (sensing and reference) is provided with a $NO_2$ sensing monolayer containing CNT terminal groups produced through chemical synthesis of the CNTs with a suitable amino alcohol, such as 4 amino-1 butanol, 5 amino 1-pentanol or 6 amino 1-hexanol.

In one embodiment, functionalization of all the Si surfaces is provided with a $NO_2$ sensing monolayer containing CNT terminal groups, together with containing CNT terminal groups bonded to downward to organic chains C=O, etc and connected to Si surface by C atoms, produced through chemical synthesis of the CNTs with a suitable unsaturated alcohol such as 3-iodo, 1-propene, 4 iodo-1 butene, 5 iodo-1 pentene.

In one embodiment, functionalization of all the Si surfaces is provided with a $NO_2$ sensing monolayer containing CNT terminal groups, together with containing CNT terminal groups bonded downward to C=0 and linked to Si surface by carbon atoms, wherein an unsaturated alcohol used for these conditions may be u 2-propen-1-ol, 3buten-1-ol or 5 penten-1-ol.

In one embodiment, functionalization of all the Si surfaces is provided with a $NO_2$ sensing monolayer containing CNT terminal group connected directly to silicon surface by $CH_2$ groups.

In one embodiment, functionalization of all the Si surfaces is provided with a $NO_2$ sensing monolayer containing ferrocene moieties.

In one embodiment, the chemical design of the functional sensing group in the sensing monolayer is based on Pearson's Hard Soft (Lewis) Acid Base (HSAB) principle. According to this theory, a hard Lewis base prefers to bond to a hard Lewis acid, and a soft Lewis base prefers to bond to a soft Lewis acid. Thus, since $NO_2$ is a soft acid, it should have a preference for a soft base. Soft bases useful herein include, but are not limited to, mercaptans, thioethers, benzene and other conjugated aromatic hydrocarbons. Other soft bases include carbon nanotubes (CNTs) and ferrocene moieties. Such molecules are considered soft bases due to their aromatic character and the reversible nature of their interactions with other charged particles. Furthermore, as a consequence of conjugation, both types of molecules can be described in terms of Kekule structures. In one embodiment, double-wall CNT's are used, due to their reduced noise, resulting in higher mass resolution and sensitivity, although the invention is not so limited. In other embodiments single-wall or multi-wall CNTs are used.

Multiple chemical routes using sequential steps are possible for providing silicon surface functionalization of both the sensing layer and the reference layer through use of soft bases. The soft bases are essentially being used as anchors for $NO_2$ sensing. By exposing the silicon surfaces from the first (sensing) beam and the second (reference) beam to the same chemical reactions, initially, the two beams are functionalized identically in a first stage, which may help in conferring similar ageing properties. However, on the reference layer, a monolayer of a compound capable of "poisoning" the sensing surface is deposited to eliminate the ability of the reference surface to function as a sensing surface, i.e., to prevent sensing from occurring on the reference beam. In one embodiment, polyethylene is applied on top of the previously functionalized surface to produce the reference layer.

Appropriate technical approaches are performed for functionalization compatibility with integrated circuit (IC) technology flow for NEMS fabrication as is known in the art. In most embodiments, care is taken to avoid allowing the suspended beam to stick to the substrate. In most embodiments, the processed substrates may be subject to treatments (such as diluted HF) in a gaseous phase rather than a liquid phase, in order to minimize the risk of suspended beam sticking to the substrate.

Route #1

In this embodiment, a silicon substrate is functionalized with a CNT moiety according to the following steps:

(1) One or more silicon (Si) substrates with exposed Si surfaces covered with native $SiO_2$ are rinsed with deionized water to produce one or more rinsed Si substrates.

(2) The one or more rinsed Si substrates are immersed in a solution of hydrogen fluoride (HF) for a period sufficient to remove native $SiO_2$ and generate a Si—H surface, thus producing one or more Si—H substrates. In one embodiment, the one or more Si—H substrates are immersed in a 2% HF solution for approximately one (1) minute:

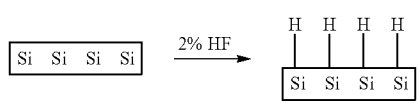

(3) The one or more H-terminated Si substrates are exposed to a stream of ozone for a time sufficient to produce one or more oxidized Si substrates, each having a hydroxyl terminated surface thereon. In one embodiment, the one or more H-terminated Si substrates are exposed for at least about five (5) minutes (min) up to about 60 min, such as about 10 to about 40 min, about 20 to about 30 min, or any range there between, such as about 24 to 26 min.

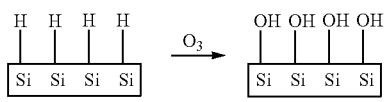

(4) The one or more oxidized Si substrates are placed in a flask containing an amino alcohol (e.g., 3 amino1-propanol) and heated in an inert atmosphere (e.g., nitrogen) for a time and at a temperature sufficient to produce one or more Si substrates, each having an amino ($NH_2$) terminated silicon surface.

In one embodiment, the one or more oxidized Si substrates are heated at a temperature of at least about 100° C., such as at least about 140 up to about 160° C., such as about 148 to about 152° C., or any range there between, for at least about two (2) (hr) up to six (6) hrs, such as about 3.5 to about 4.5 hrs, or any range there between, further including about four (4) hrs.

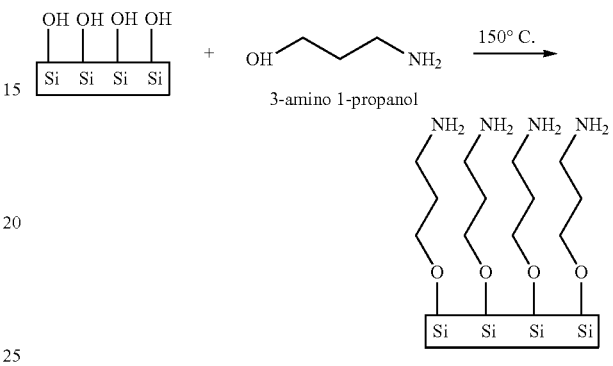

(5) After the condensation reaction, the one or more Si substrates are rinsed with an unsaturated alcohol, such as isopropyl alcohol, deionized water and dried under a nitrogen stream to produce one or more processed Si substrates, with each of the one or more processed Si substrates having a rinsed and dried $NH_2$ terminated silicon surface:

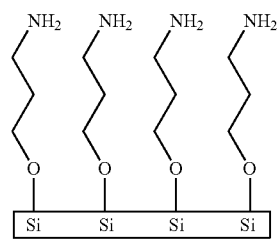

(6) Separately, one or more CNTs are sonicated in a mixture of nitric acid and sulfuric acid at a suitable ratio (e.g., 1:3) at a frequency, power and duration sufficient to functionalize the one or more CNTs with a carboxylic group to produce one or more carboxylic CNTs:

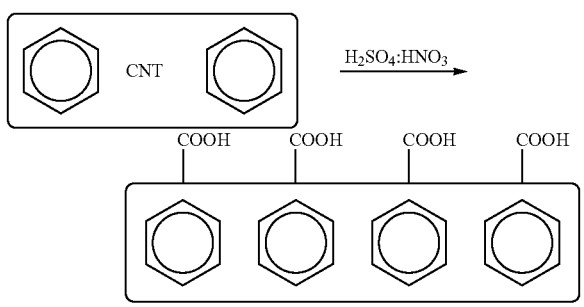

(7) The one or more carboxylic CNTs are mixed with tionyl chloride ($SOCl_2$) in an amount sufficient to convert the carboxylic acid moieties to carboxylic chloride moieties to produce one or more COCl-CNTs:

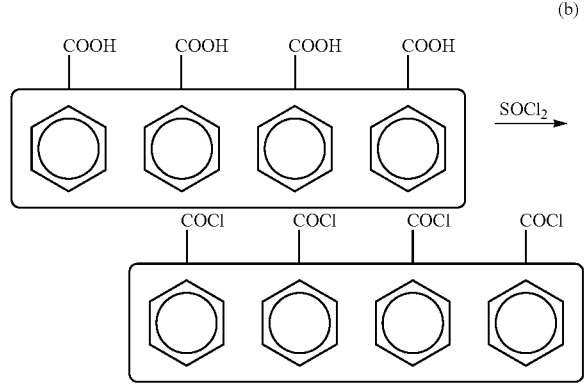

(8) The one or more CNT-COCls (b) are reacted with the one or more Si substrates (a) having rinsed and dried NH$_2$ terminated silicon surfaces (from Step #5) to produce one or more Si substrates coated or functionalized with one or more CNT moieties for NO$_2$ detection:

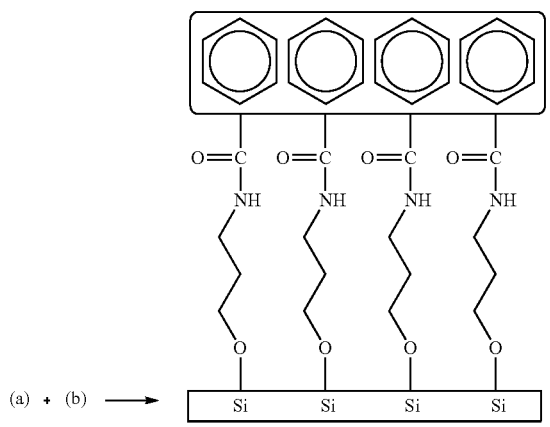

No further processing is performed on the substrates to be used as sensing beams.

(9) For CNT-coated Si substrates intended for use as reference beams, however, selective direct printing of a monolayer of polyethylene on top of each of the one or more CNT-coated substrates is performed, thereby eliminating the ability of the reference beam to sense NO$_2$.

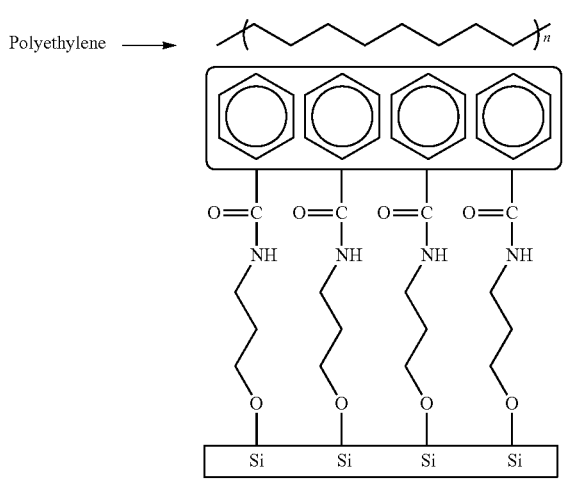

Route #2

In this embodiment, a silicon substrate is functionalized with a CNT moiety by an alternate method. The process proceeds as outlined in Steps 1 and 2 above. Thereafter:

(3) The one or more H-terminated Si substrates are combined with a suitable amount of an allyl iodide and heated in a non-polar solvent, such as toluene, at a ratio and for a time and at a temperature sufficient to produce one or more iodine terminated (functionalized) Si substrates.

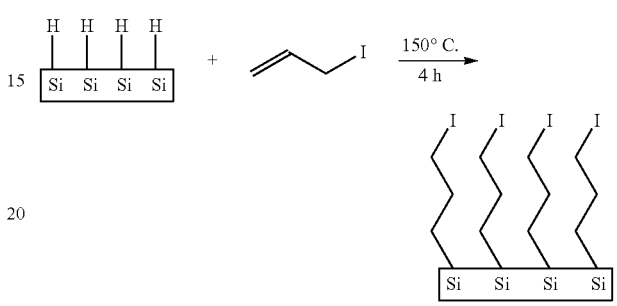

In one embodiment, the one or more H-terminated Si substrates are heated at a temperature of at least about 100° C., such as at least about 140 up to about 160° C., such as about 148 to about 152° C., or any range there between, for at least about two (2) (hr) up to six (6) hrs, such as about 3.5 to about 4.5 hrs, or any range there between, further including about four (4) hrs.

(4) The one or more iodine terminated (functionalized) Si substrates are cooled in ambient conditions down to room temperature.

(5) The one or more iodine terminated (functionalized) Si substrates are rinsed with a suitable unsaturated alcohol, such as ethanol and deionized water dried under nitrogen stream=to produce one or more processed Si substrates, with each of the one or more processed Si substrates having a rinsed and dried iodine-terminated silicon surface:

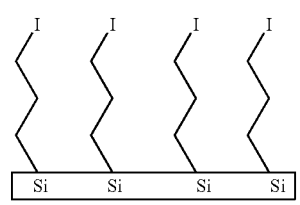

(6) Separately (as in Step (6) of Route #1 above), one or more CNTs are sonicated in a mixture of nitric acid and sulfuric acid at a suitable ratio (e.g., 1:3) at a frequency, power and duration sufficient to functionalize the one or more CNTs with a carboxylic group to produce one or more carboxylic CNTs:

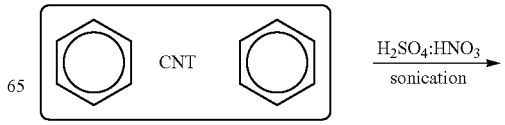

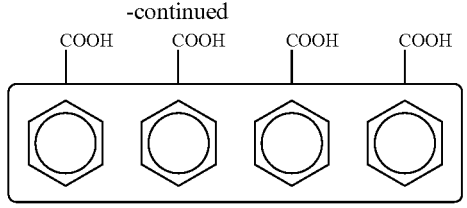

7) The one or more carboxylic CNTs are sonicated in a suitable amount of sodium hydroxide (NaOH) at a frequency, power and duration sufficient to form one or more sodium salt CNTs:

(b)

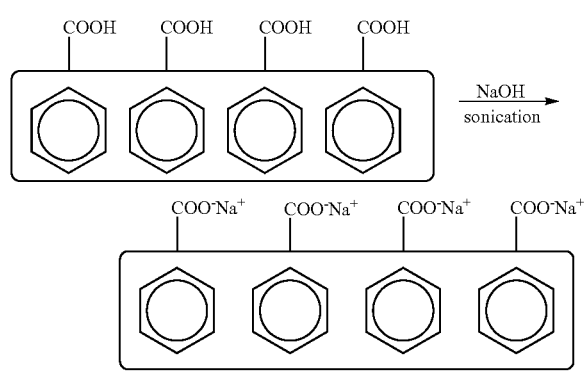

8) The one or more sodium salt CNT's (b) are reacted with the one or more Si substrates (a), each having rinsed and dried iodine-terminated silicon surfaces (from Step #5) in the presence of a sufficient amount of a phase transfer catalyst (e.g., tetramethylammonium iodide) at a temperature in the range of 40-60° C. sufficient to produce one or more Si substrates coated or functionalized with one or more CNT moieties for $NO_2$ detection:

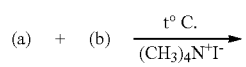

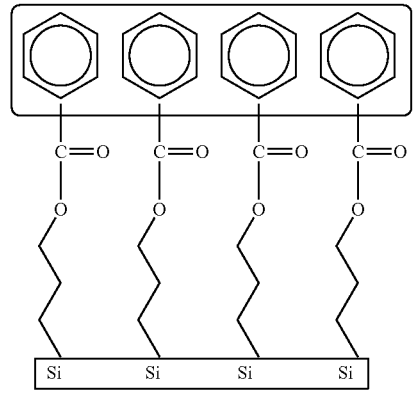

No further processing is performed on the substrates to be used as sensing beams.

(9) For CNT-coated Si substrates intended for use as reference beams, selective direct printing of a monolayer of polyethylene on top of each of the one or more CNT-coated substrates is performed.

Route #3

In this embodiment, a silicon substrate is functionalized with a CNT moiety by an alternate method. The process proceeds as outlined in Steps 1 and 2 above. Thereafter:

(3) The one or more H-terminated Si substrates are combined with an allyl alcohol protected with benzyl groups in a suitable non-polar solvent, such as toluene, under conditions sufficient to produce one or more OH-terminated silicon substrates:

(a)

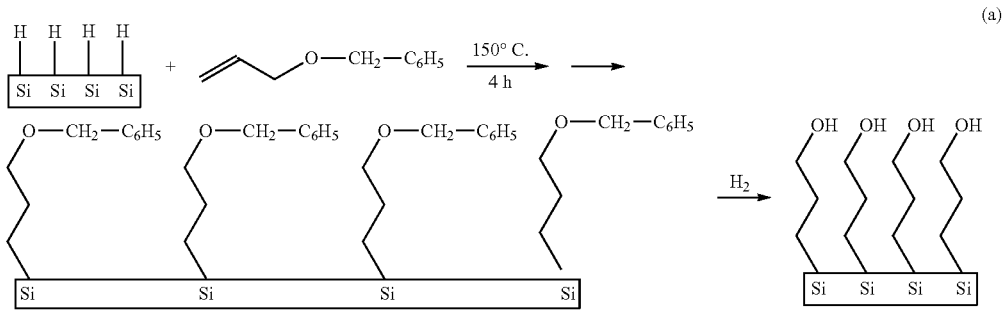

In one embodiment, the one or more H-terminated Si substrates are heated to a temperature of 100° C., such as at least about 140 up to about 160° C., such as about 148 to about 152° C., or any range there between, for at least about two (2) (hr) up to six (6) hrs, such as about 3.5 to about 4.5 hrs, or any range there between, further including about four (4) hrs.

(4) The one or more functionalized Si substrates are cooled under ambient conditions down to room temperature.

(5) The one or more cooled functionalized Si substrates are rinsed with an alcohol, such as ethanol and deionized water dried under nitrogen stream to produce one or more processed Si substrates:

(6) Deprotection of the alcohol is accomplished through hydrogenation according to the same reactions shown in Step 3 to produce one or more processed Si substrates:

(7) Separately (as in Step (6) of Route #1 above), one or more CNTs are sonicated in a mixture of nitric acid and sulfuric acid at a suitable ratio (e.g., 1:3) at a frequency, power and duration sufficient to functionalize the one or more CNTs with a carboxylic group to produce one or more carboxylic CNTs:

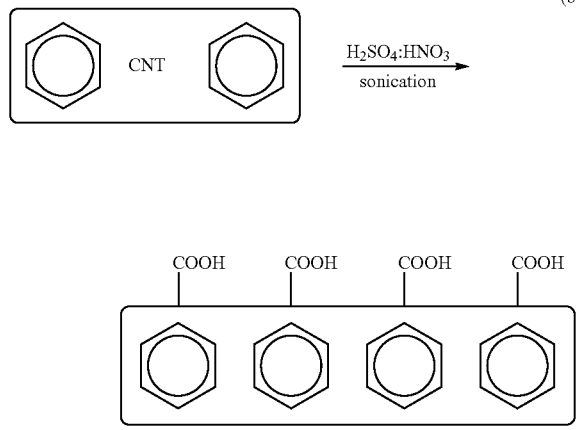

(8) The one or more carboxylic CNTs (b) are reacted with the one or more Si substrates (a) having rinsed and dried functionalized silicon surfaces (from Step #6) in the presence of a dicyclohexyl carbodiimide (DCC) in DMSO, at a temperature, such as 40-60° C., sufficient to produce one or more Si substrates coated or functionalized with one or more CNT moieties for $NO_2$ detection. No further processing is performed on the substrates to be used as sensing beams:

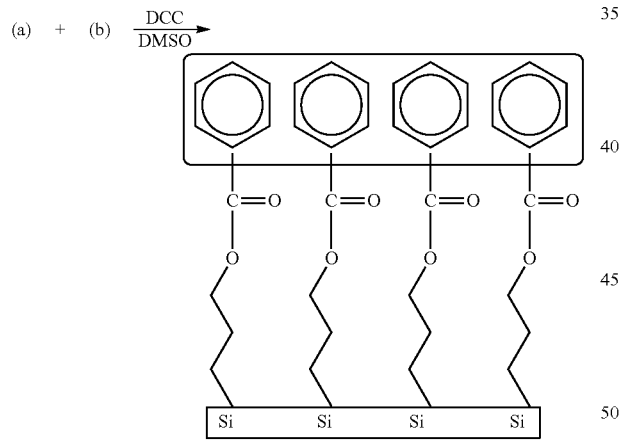

(9) For CNT-coated Si substrates intended for use as reference beams, selective direct printing of a monolayer of polyethylene on top of each of the one or more CNT-coated substrates is performed.

Route #4

In this embodiment, a silicon substrate is functionalized with a CNT moiety by yet another alternate method. The process proceeds as outlined in Steps 1 and 2 above. Thereafter:

(3) The one or more H-terminated Si substrates are combined with an allyl iodide and potassium in a high-speed vibration mill under conditions sufficient to produce one or more H-terminated Si substrates.

(4) In one embodiment, the one or more H-terminated Si substrates synthesized in step 3 are heated in a non-polar solvent, such as toluene under conditions sufficient to produce one or more functionalized silicon substrates.

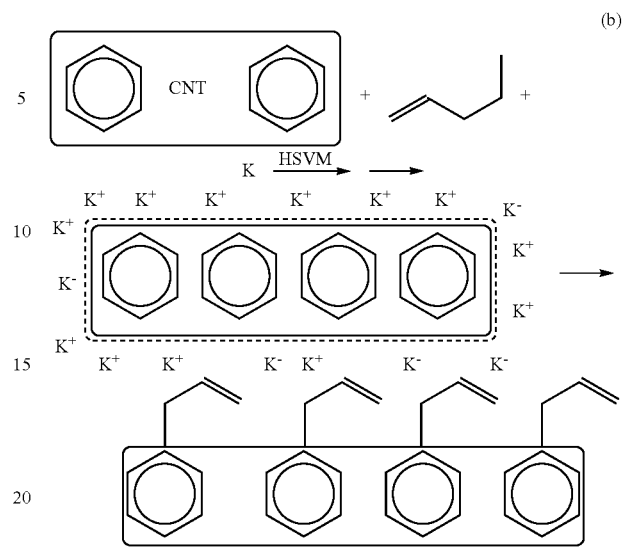

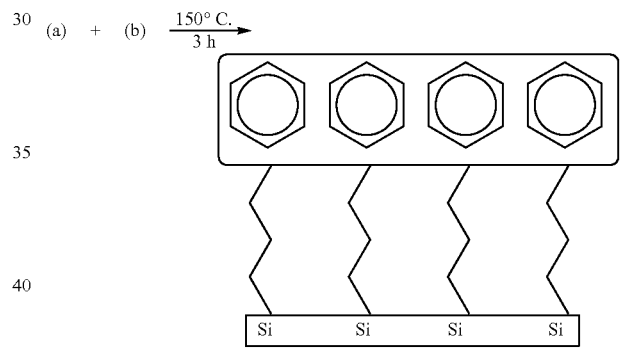

In one embodiment, the mixture is heated to a temperature of a 100° C., such as at least about 140 up to about 160° C., such as about 148 to about 152° C., or any range there between, for at least about two (2) (hr) up to six (6) hrs, such as about 3.5 to about 4.5 hrs, or any range there between, further including about four (4) hrs.

(5) The one or more functionalized Si substrates are cooled in ambient conditions down to room temperature.

(6) The one or more functionalized Si substrates are rinsed with an alcohol, such as ethanol and deionized water dried under nitrogen stream-to produce one or more dried processed Si substrates.

For functionalized Si substrates intended for use as reference beams, selective direct printing of a monolayer of polyethylene on top of each of the one or more CNT-coated substrates is performed.

Route #5

In this embodiment, a silicon substrate is functionalized with a ferrocene moiety. The process proceeds as outlined in Steps 1 and 2 above. for getting a hydrogen terminated silicon surface Thereafter:

(3) In one embodiment, the one or more H-terminated Si substrates synthesized in step 2 are combined with vinyl ferrocene together with a non-polar solvent, such as toluene, under conditions sufficient to produce one or more functionalized silicon substrates.

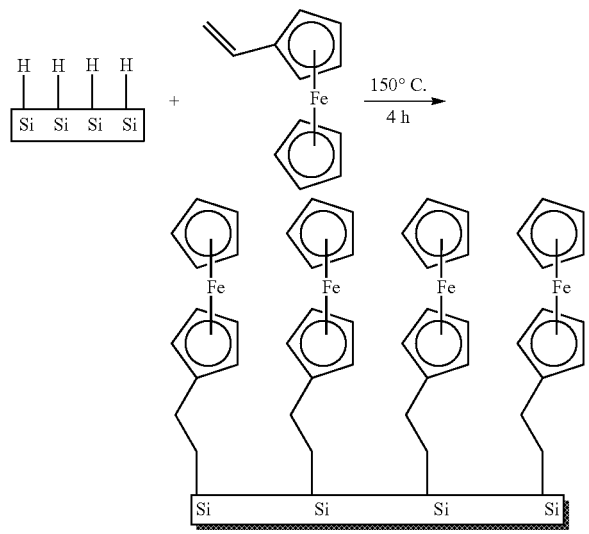

In one embodiment, the mixture is heated to a temperature of a 100° C., such as at least about 140 up to about 160° C., such as about 148 to about 152° C., or any range there between, for at least about two (2) (hr) up to six (6) hrs, such as about 3.5 to about 4.5 hrs, or any range there between, further including about four (4) hrs.

(5) The one or more functionalized Si substrates are cooled in ambient conditions down to room temperature.

(6) The one or more functionalized Si substrates are rinsed with an alcohol, such as ethanol and deionized water and dried under nitrogen stream to produce one or more dried and processed Si substrates.

For functionalized Si substrates intended for use as reference beams, selective direct printing of a monolayer of polyethylene on top of each of the one or more ferrocene-containing Si substrates is performed.

CONCLUSION

A novel a low cost, high performance $NO_2$ gas sensor is provided which uses resonant differential principles. In one embodiment, this technology is applied to silicon nano-electromechanical systems (NEMS). In one embodiment, a vibrating functionalized nano-beam changes resonance frequency as a function of $NO_2$ gas concentration in the ambient air.

Although specific embodiments have been illustrated and described herein, it will be appreciated by those of ordinary skill in the art that any procedure that is calculated to achieve the same purpose may be substituted for the specific embodiments shown. This application is intended to cover any adaptations or variations of the present subject matter. Therefore, it is manifestly intended that embodiments of this invention be limited only by the claims and the equivalents thereof.

The Abstract is provided to comply with 37 C.F.R. §1.72(b) is submitted with the understanding that it will not be used to interpret or limit the scope or meaning of the claims.

What is claimed is:

1. A nitrogen dioxide sensor comprising:
   a first beam having a first functionalized sensing surface capable of sensing nitrogen dioxide, the first beam capable of producing a first resonant frequency; and
   a second beam having a second functionalized reference surface not capable of sensing nitrogen dioxide, the second beam capable of producing a second resonant frequency, wherein differential sensing of nitrogen dioxide may be performed, further wherein the first beam and the second beam are each functionalized with one or more soft bases having comparable viscoelastic properties.

2. The sensor of claim 1 wherein the second functionalized reference surface is altered with a polyethylene coating to prevent detection of nitrogen dioxide.

3. The sensor of claim 2 comprising a nano sensor capable of performing differential sensing by monitoring changes in the resonant frequency of the first beam relative to the resonant frequency of the second beam.

4. The sensor of claim 3 wherein the first beam and the second beam are located on a single silicon substrate.

5. The sensor of claim 3 wherein the first beam and the second beam are located on different silicon substrates.

6. The sensor of claim 1 wherein the one or more soft bases are selected from a conjugated aromatic hydrocarbon, a carbon nanotube, and a ferrocene moiety.

7. The sensor of claim 6 wherein the functionalized surface of the first beam contains carbon nanotube moieties as sensitive groups for nitrogen dioxide detection bonded downward to C=O and linked to the functionalized surface by carbon atoms and the functionalized surface of the second beam further contains a coating of polyethylene to prevent detection of nitrogen dioxide.

8. The sensor of claim 6 wherein the functionalized surface of the first beam contains ferrocene moieties as sensitive groups for nitrogen dioxide detection, and the functionalized surface of the second beam further contains a coating of polyethylene to prevent detection of nitrogen dioxide.

9. The sensor of claim 8, further comprising:
   a first frequency measuring circuit for measuring the resonant frequency of the first beam;
   a second frequency measuring circuit for measuring the resonant frequency of the second beam: and
   a control for analyzing the signals from the first frequency measuring circuit and the second frequency measuring circuit, wherein a differential frequency equivalent to the first frequency minus the second frequency is determinable, wherein differential sensing of nitrogen dioxide exposure is performed.

10. The sensor of claim 6 comprising a low drift sensor capable of detecting nitrogen dioxide levels up to a zeptogram level.

11. The sensor of claim 1 wherein the first beam is functionalized with a first soft base and the second beam is functionalized with a second soft base.

12. A method comprising:
   functionalizing a silicon surface with a first soft base to detect nitrogen dioxide; and
   altering a portion of the functionalized silicon surface with a second soft base to prevent detection of nitrogen dioxide, wherein the second soft base has viscoelastic properties comparable to the first soft base.

13. The method of claim 12 wherein the silicon surface is functionalized with carbon nanotube moieties by first preparing an amino-terminated silicon surface or an iodine-terminated silicon surface.

14. The method of claim 12 wherein the silicon surface is functionalized through reaction of carboxylic carbon nanotubes with an alcohol-terminated silicon surface n the presence of dicyclohexil carbodiimide in DMSO.

15. The method of claim 12 wherein the silicon surface is functionalized through reaction of a compound synthesized by reacting carbon nanotubes with allyl iodide and potassium and hydrogen terminated silicon surfaces.

16. The method of claim 12 wherein the altering step comprises direct printing of a polyethylene coating on the portion of the functionalized silicon surface.

17. The method of claim 16 further comprising:
connecting frequency measuring devices to the silicon surface to produce differential resonant frequency changes;
connecting a mixer to the frequency measuring devices to measure the differential resonant frequency changes; and
outputting the differential resonant frequency changes to a presentation device.

18. The method of claim 12 wherein the silicon surface is a silicon wafer.

19. A method of detecting nitrogen dioxide comprising:
exposing first and second beams the silicon surface to nitrogen dioxide, wherein the first beam has a functionalized surface to detect nitrogen dioxide and the second beam has a functionalized surface altered to prevent detection of nitrogen dioxide; and
comparing the resonant frequency of the first beam silicon surface functionalized with a first soft base to the resonant frequency of second beam the portion of the functionalized silicon surface altered with the second soft base, wherein an amount of carbon nitrogen dioxide exposure is determined.

20. The method of claim 19 wherein the first and second beams functionalized silicon surfaces are nano-beams and the second beam second soft base is altered with a polyethylene coating.

21. The method of claim 20 wherein the first and second soft bases each comprise one or more soft bases.

22. The method of claim 21 wherein the one or more soft bases are selected from a conjugated aromatic hydrocarbon, a carbon nanotube, a ferrocene moiety, and combinations thereof.

* * * * *